US009655714B1

(12) United States Patent
Hovis

(10) Patent No.: US 9,655,714 B1
(45) **Date of Patent: *May 23, 2017**

(54) ARTHROSCOPIC TENODESIS TOOL

(71) Applicant: W. David Hovis, Knoxville, TN (US)

(72) Inventor: W. David Hovis, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/935,651

(22) Filed: Nov. 9, 2015

Related U.S. Application Data

(63) Continuation-in-part of application No. 13/896,460, filed on May 17, 2013, now Pat. No. 9,277,951.

(51) Int. Cl.
*A61B 17/88* (2006.01)
*A61F 2/08* (2006.01)
*A61B 17/90* (2006.01)
*A61B 17/04* (2006.01)

(52) U.S. Cl.
CPC ........ *A61F 2/0811* (2013.01); *A61B 17/8875* (2013.01); *A61B 17/0401* (2013.01); *A61B 2017/044* (2013.01); *A61B 2017/0409* (2013.01); *A61B 2017/0445* (2013.01); *A61B 2017/90* (2013.01); *A61F 2002/0841* (2013.01); *A61F 2002/0858* (2013.01); *A61F 2002/0882* (2013.01)

(58) Field of Classification Search
CPC ........ A61F 2/08; A61F 2/0811; A61F 2/0805; A61B 17/04
USPC .................................................. 606/232, 233
See application file for complete search history.

(56) References Cited

U.S. PATENT DOCUMENTS 5,098,435 A 3/1992 Stednitz et al.
5,439,467 A 8/1995 Benderev et al.
6,319,257 B1 11/2001 Carignan et al.
6,461,373 B2 10/2002 Wyman et al.
6,544,281 B2 4/2003 ElAttrache et al.
7,815,654 B2 10/2010 Chu
7,857,817 B2 12/2010 Talloarida et al.
2002/0065528 A1 5/2002 Clark et al.
2002/0161439 A1* 10/2002 Strobel .............. A61B 17/0401 623/13.14
2003/0139754 A1* 7/2003 Schmieding ......... A61B 17/064 606/151
2005/0288682 A1 12/2005 Howe
2008/0004659 A1* 1/2008 Burkhart ............ A61B 17/0401 606/232
2009/0069846 A1* 3/2009 Bull ................... A61B 17/0469 606/228
2009/0287259 A1 11/2009 Trenhaile et al.
2010/0145395 A1 6/2010 Graf et al.
2011/0106253 A1* 5/2011 Barwood .............. A61F 2/0811 623/13.14
2012/0123473 A1 5/2012 Hernandez
2012/0226355 A1 9/2012 Baird
(Continued)

*Primary Examiner* — Christopher Beccia
(74) *Attorney, Agent, or Firm* — Luedeka Neely Group, PC

(57) ABSTRACT

An arthroscopic tenodesis kit, includes a guide provided by an elongate member having a length with a distal portion having a plurality of angled slots configured to directly and releasably engage a tendon. The kit also includes an inserter with an elongate cannulated body having an interior bore having a blind end and an open end configured to slidingly receive the guide. The body of the inserter has a length that is shorter than the length of the guide, so that the distal portion of the guide remains spaced from the bore when the guide is fully received within the bore.

8 Claims, 8 Drawing Sheets

16a
12
16
32
14
30
34

(56) References Cited

U.S. PATENT DOCUMENTS

2013/0079817 A1 3/2013 Sengun et al.
2013/0237997 A1 * 9/2013 Arai .................. A61B 17/0401
606/144

* cited by examiner

ARTHROSCOPIC TENODESIS TOOL

CROSS-REFERENCE TO RELATED APPLICATION

This application claims priority to co-pending U.S. application Ser. No. 13/896,460 filed May 17, 2013, entitled ARTHROSCOPIC TENODESIS TOOL, and incorporated herein by reference in its entirety.

FIELD

This disclosure relates generally to methods and apparatus for fixation of a tendon to bone. More particularly, this disclosure relates to arthroscopic methods and apparatus for fixation of a tendon to bone without the need to secure a suture to the tendon.

BACKGROUND

Improvement is desired in the field of tenodesis or surgical fixation or anchoring of tendons to bone. Improvement is particularly desired in regards to arthroscopic fixation of tendons to bone.

Current devices often require a dedicated interference screw or fixation device and cannot be used with a wide variety of cannulated interference screws. Current devices also are hampered by the large size of the inserter and implant assembly that blocks arthroscopic view of the tunnel and impedes surgeon performance. Currently available devices also do not enable temporary fixation of the tendon to bone prior to implant insertion. Therefore, the tendon has a tendency to wrap around the interference screw as it is being inserted. This makes insertion of the screw more complex and also impedes visibility of the surgeon. Alternatively, current devices undesirably utilize a second separate implant (other than the fixation screw) which adds cost to the procedure, and is undesirable in that a second implant remains in the body after the procedure.

The disclosure advantageously provides apparatus and methods for arthroscopic tenodesis that does not require a dedicated interference screw or fixation device, but is suitable for use with a wide variety of cannulated interference screws. The apparatus and methods according to the disclosure also advantageously enable temporary distal fixation to the bone, avoid the need for any implant beyond the fixation screw, improve surgeon visibility, and reduce operating room time and costs by reducing the number of steps required as compared to conventional tenodesis procedures.

The apparatus and the methods disclosed also further reduce the number of steps and provide a simplified tenodesis procedure by eliminating the need to attach a suture to the tendon.

SUMMARY

The present disclosure relates to methods and apparatus for arthroscopic tenodesis.

In one aspect, there is disclosed an arthroscopic guide for use in installing a cannulated fixation screw for attaching a tendon to a bone. The guide is provided by an elongate member having a length with a distal portion having a plurality of angled slots configured to directly and releasably engage a tendon.

A kit is provided that includes the guide and an inserter with an elongate cannulated body having an interior bore having a blind end and an open end configured to slidingly receive the guide. The body of the inserter has a length that is shorter than the length of the guide, so that the distal portion of the guide remains spaced from the bore when the guide is fully received within the bore.

In other aspects of the disclosure, methods are provided for performance of an arthroscopic tenodesis procedure without the need to utilize suture material for attaching the tendon to bone.

BRIEF DESCRIPTION OF THE DRAWINGS

Further advantages of the disclosure are apparent by reference to the detailed description in conjunction with the figures, wherein elements are not to scale so as to more clearly show the details, wherein like reference numbers indicate like elements throughout the several views, and wherein.

DETAILED DESCRIPTION

The disclosure describes an arthroscopic tenodesis tool 10 having a guide 12 and an inserter 14. The tool 10 advantageously enables performance of an arthroscopic tenodesis procedure without the need to utilize suture material for attaching the tendon to bone.

In brief overview, the guide 12 is configured to releasably engage a tendon to be affixed to a bone with a fastener, such as a screw. The inserter 14 telescopically receives the guide 12 that serves to stiffen the guide 12 for inserting the guide 12 into the bone for desirably positioning the tendon to the bone. The inserter 14 is then removed and the guide 12 is utilized to guide a cannulated interference screw to the site for installation, with the guide 12 thereafter being withdrawn in its entirety, such that only the tendon and the interference screw remain in the patient at the conclusion of the procedure.

The guide 12 is provided as by an elongate rod 16 having a distal portion **16*a* configured to releasably engage a tendon. The rod 16 is preferably of solid construction and has a length of from about 200 mm to about 375 mm and a diameter of from about 1 mm to about 3 mm. The diameter of the rod 16 is desirably small enough to enable commonly available cannulated fixation screws to receive the rod 16. Thus, the rod 16 preferably has an outer diameter or outer major dimension of no more than about 1.6 mm so as to be receivable by commonly available cannulated fixation screws. The rod 16 is preferably of circular cross-section, but may be of other cross section. The rod 16 is made of a surgically compatible material, such as stainless steel. Because the outer major dimension of the rod 16 is relatively small compared to the length of the rod 16, the rod 16 tends to flex. Thus, as described below, the inserter 14 is provided for use with the guide 12 to add rigidity in inserting the guide 12**.

Figure 3:
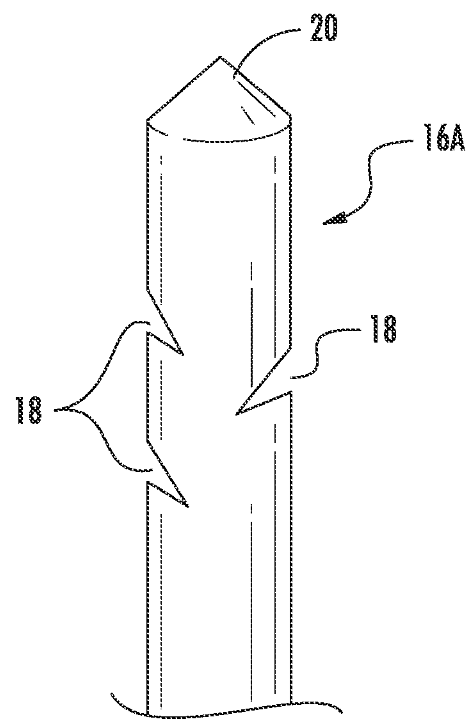
FIG. 3 is an enlarged view of a distal end of a guide component of the tool of FIG. 1.
Figure 4:
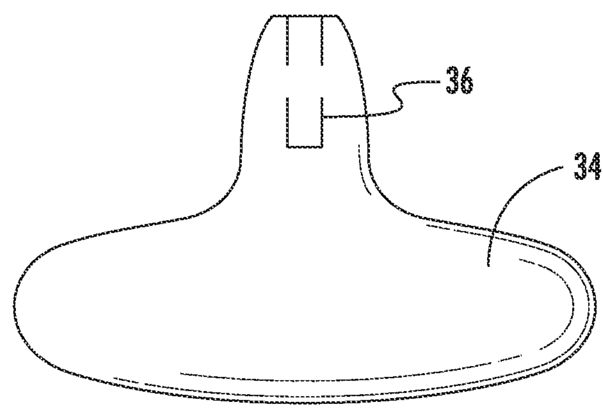
FIG. 4 shows a handle of an inserter component of the tool of FIG. 1.

With reference to FIG. 3, an enlarged view of the distal portion 16*a* of the rod 16 is shown. The distal portion 16*a* defines a plurality of angled slots 18 that open toward the free end of the distal portion 16*a*. The end of the distal portion 16*a* of the rod 16 is desirably configured to provide a point 20 that can be imbedded into bone.

The slots 18 are configured as acute angles, preferably opening at an angle of from about 45 to about 70 degrees. The slots are preferably staggered on opposite sides of the distal portion 16*a*. For example, in a preferred embodiment three of the slots 18 are provided and staggered on opposite sides, with one of the slots 18 on one side and two of the slots 18 on the other side. The two slots 18 on one side are spaced so that the one slot 18 on the opposite side is aligned between the two slots 18. The slots 18 are thus configured to releasably hold a portion of the tendon and to permit the tendon to be pushed toward the bone. This configuration of the slots 18 advantageously enables a portion of the tendon to be frictionally retained by the slots 18, yet subsequently released when desired.

Figure 14:
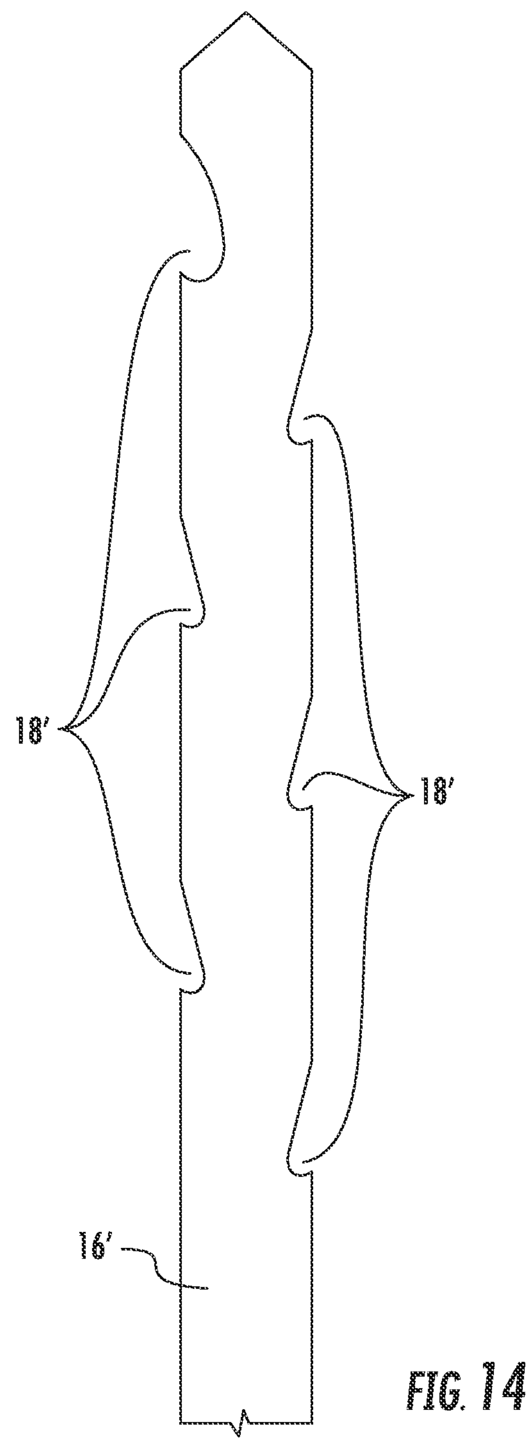
FIG. 14 shows an enlarged view of a distal end of an alternate embodiment of a guide component.

In another preferred embodiment, six or more slots of various depths are present on each side and staggered such that no slot is exactly opposite another. For example, FIG. 14 shows a rod 16' having six slots 18', with three of the slots 18' on each side and staggered such that none of the slots 18' is exactly opposite another.

For the purpose of example only, each slot 18 is dimensioned and configured so that the notch is to a depth that captures tendinous tissue but maintains adequate yield strength and flexural strength of the rod to avoid breakage or deformation. Notches may all be the same depth, or various depths. In a preferred embodiment the notch depth is about 0.6 mm.

Figure 1:
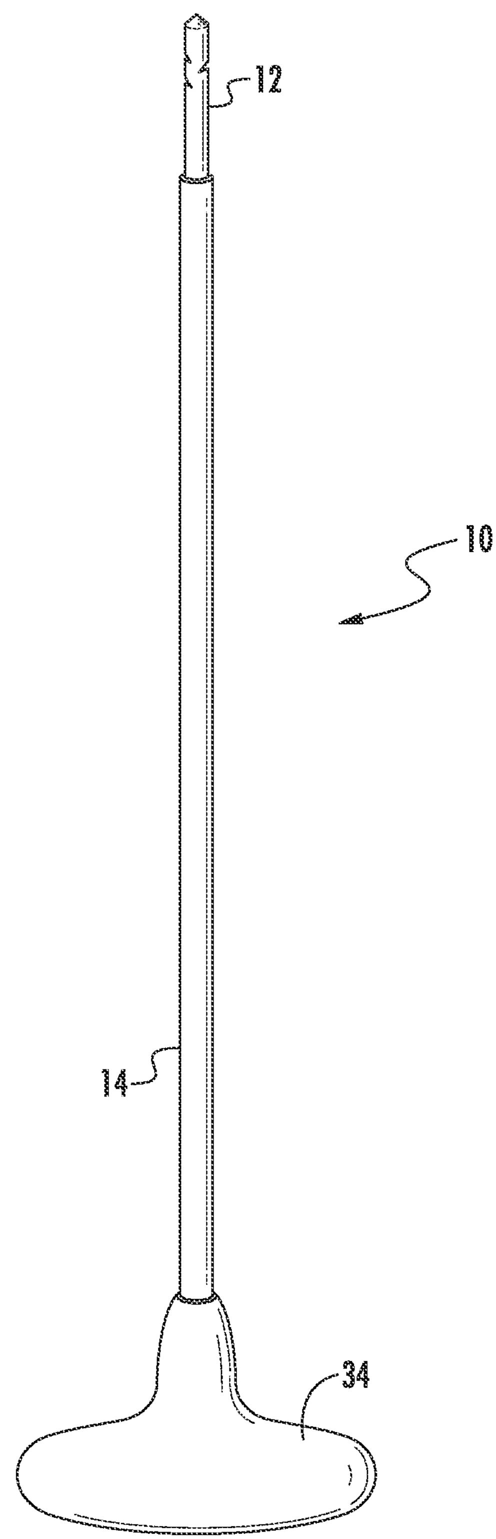
FIG. 1 shows a tenodesis tool according to the disclosure.
Figure 2:
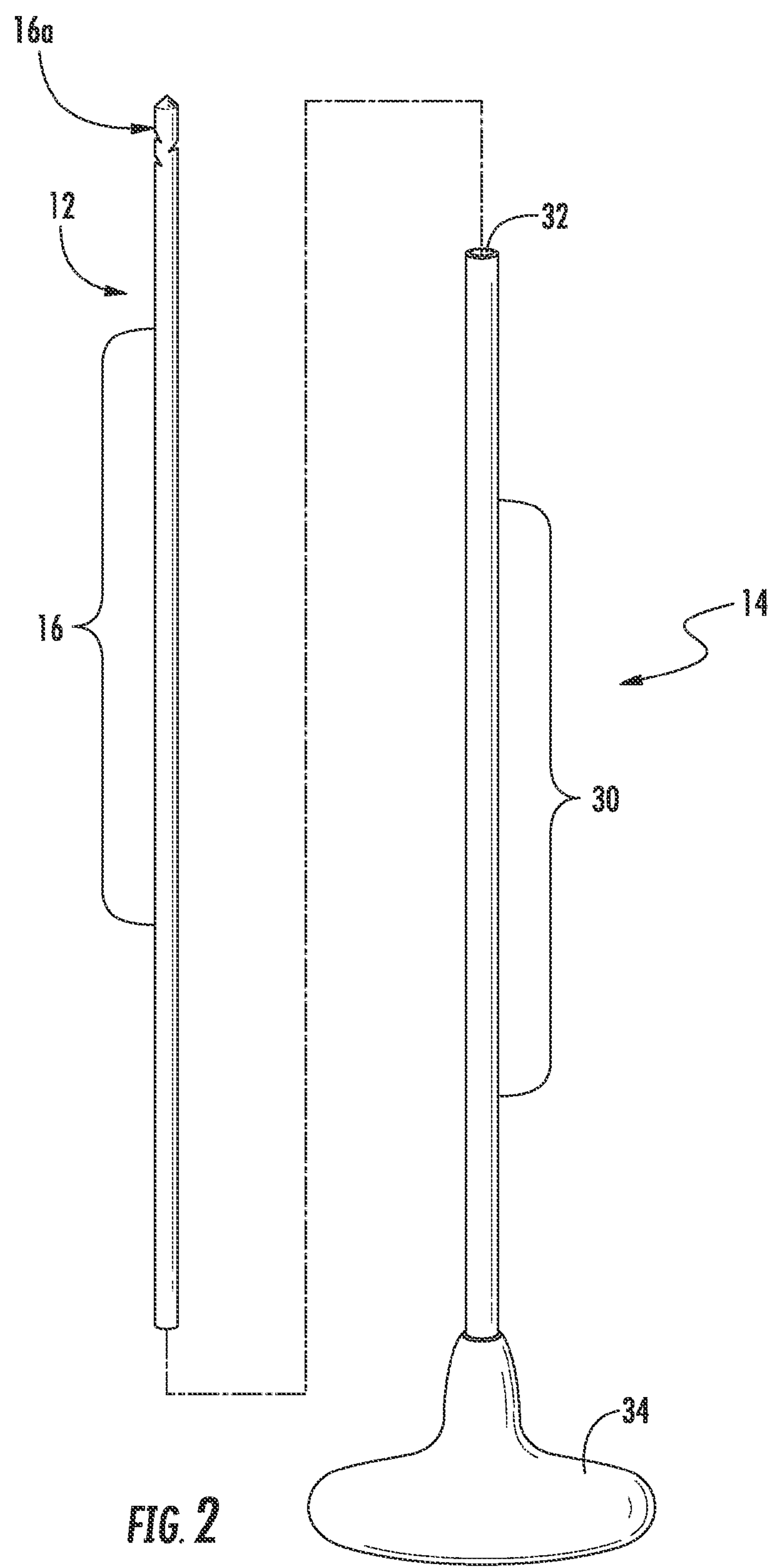
FIG. 2 shows an exploded view of the tool of FIG. 1.

The inserter 14 is provided by an elongate cannulated or cylindrical body 30 having a uniform interior bore 32 configured to slidingly receive the guide 12. The body 30 of the inserter 14 has a length that is shorter than the length of the guide 12, preferably from about 10 to 25 mm shorter, most preferably from about 15 to 20 mm shorter. Thus, as shown in FIG. 1, when the guide 12 is fully received by the inserter 14, the notch 18 is exposed.

The distal end of the body 30 receives the proximal end of the rod 16. The proximal end of the body 30 is seated in a T-shaped handle 34. For example, the handle 34 may be configured to have a blind bore 36 that retains the rod 16. The interior bore 32 may have a blind end adjacent the blind bore 36 of the handle, or the blind bore 36 of the handle 34 may serve to provide a blind end for the interior bore. Thus, the distal portion of the guide 12 remains spaced from the open end of the inserter 14 when the guide 12 is fully received by the inserter 14. The bore 36 may be of adjustable depth. This is advantageous to allow the surgeon to adjust the amount that the rod 16 extends from the inserter 14 and thereby select how deep the distal end is embedded in the bone.

The inserter 14 functions to stiffen the rod 16, as the rod 16 is of a small diameter due to the cannulation diameter of interference screws with which it is intended to be used. The interior bore 32 preferably has a diameter of from about 2 mm to about 3 mm. The exterior diameter of the cylindrical body 30 is preferably from about 2.5 mm to about 4 mm, such that the sidewall of the cylindrical body 30 is sufficient to provide strength against bending during use, such as when hammering the guide 12 into the bone, as described more fully below. Both the cylindrical body 30 and the handle 34 are made of a strong and surgically compatible material, such as stainless steel.

The tool 10 is particularly configured for use in an arthroscopic bicep tenodesis procedure according to the disclosure and depicted in FIGS. 5-11. In overview, the tendon T is delivered using the tool 10 into a bony tunnel or socket. The tool 10 then is used to facilitate passage of a fixation screw for fixation of the tendon in the tunnel or socket. The procedure accomplished using the tool 10 advantageously facilitates joinder of the tendon to the bone, and installation of the fixation screw and avoids rotation or winding of the tendon around the screw as it is inserted.

Figure 5:
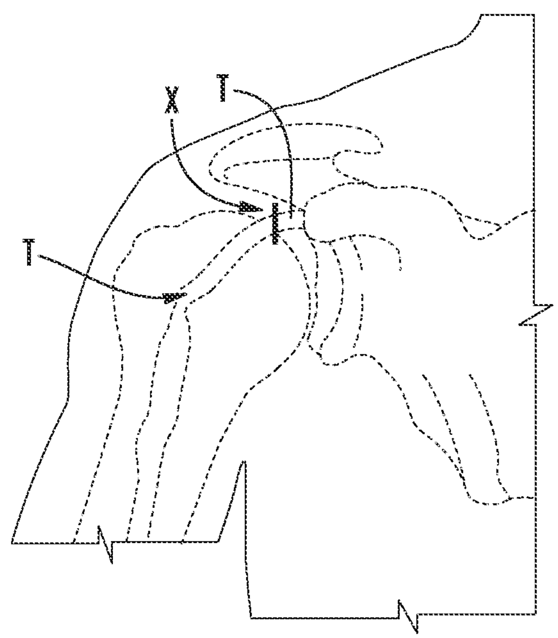
FIGS. 5-11 show steps in accomplishing a bicep tenodesis arthroscopic procedure utilizing the tool of FIG. 1 in accordance with the disclosure.

With reference to FIG. 5, in an initial step according to the disclosure, there is shown a shoulder joint with a biceps tendon T, and the surgeon will arthroscopically cut the biceps tendon T at location designated generally by reference character X.

Figure 6:
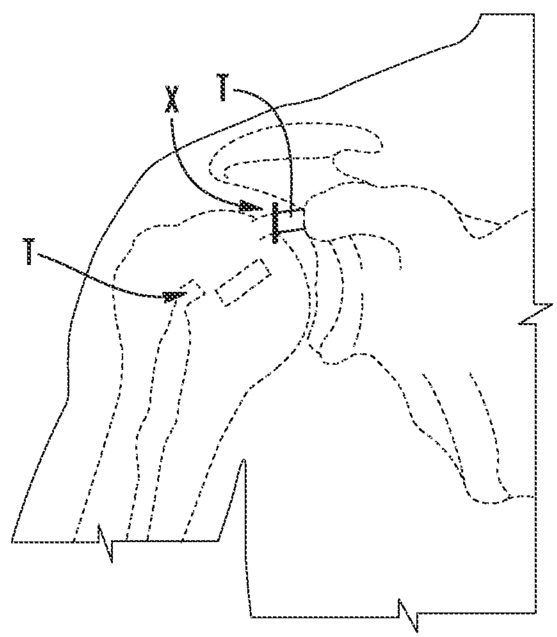

Turning to FIG. 6, the surgeon will also form a tunnel or channel C into a bone B, such as the humerus bone of the shoulder, as by use of a drill or reamer.

Figure 7:
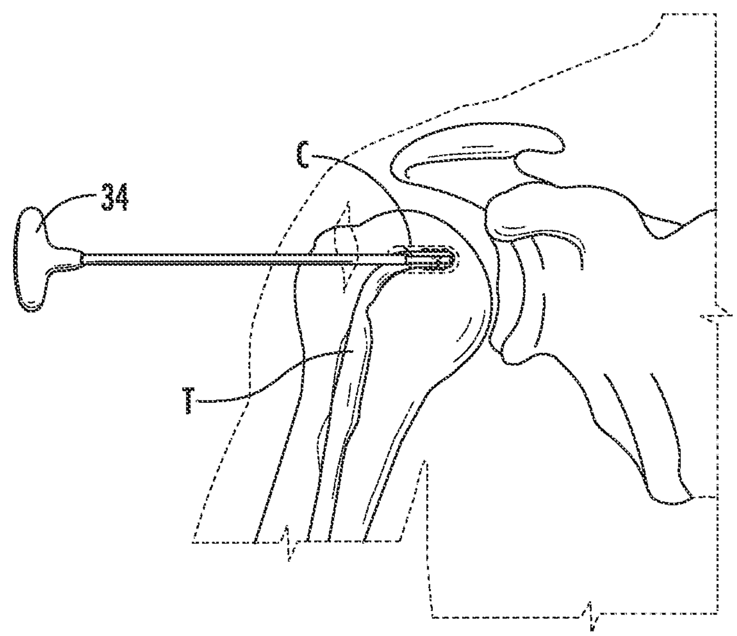

Next, as shown in FIG. 7, the tool 10 with the biceps tendon captured in the slots 18, is manipulated to urge the biceps tendon T into and down the channel C to a desired location within the bone B. A hammer or the like is preferably used to pound on the handle 34 of the inserter 14 to drive and imbed the distal end of the guide 12 adjacent the distal portion 16*a* into the bone B at the desired location to temporarily locate the distal end of the guide 12 in the bone B.

Figure 8:
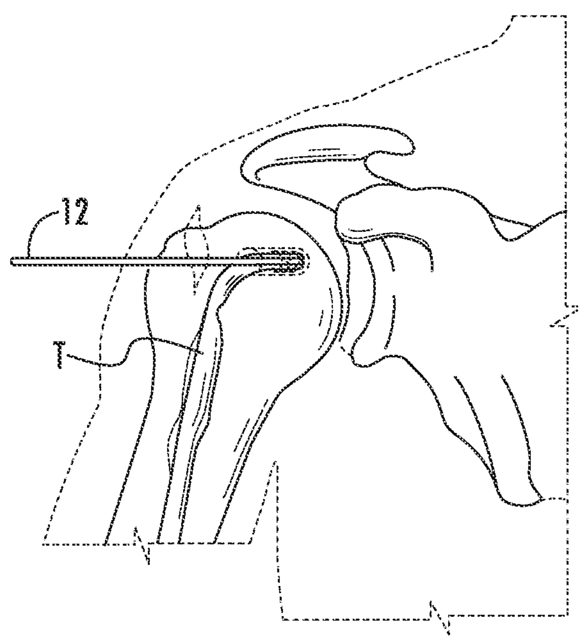
Figure 9:
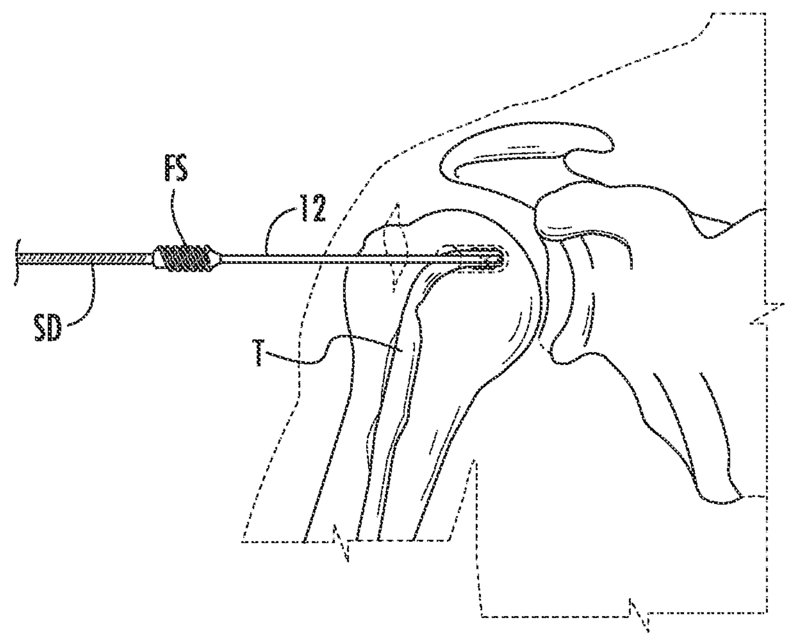
Figure 10:
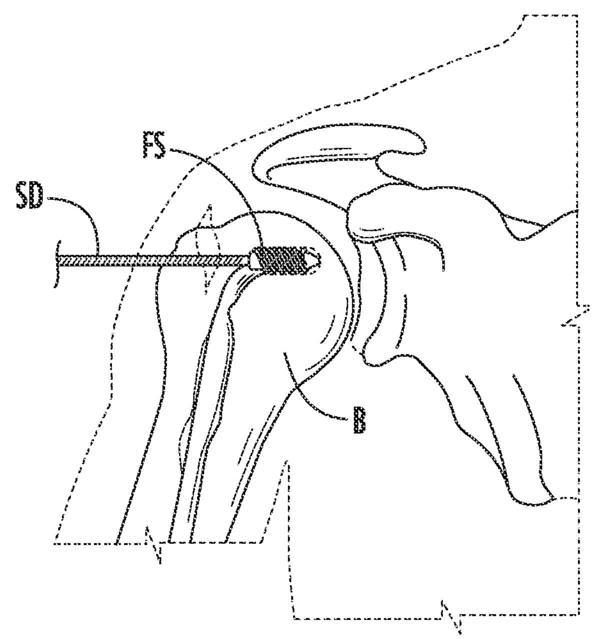
Figure 11:
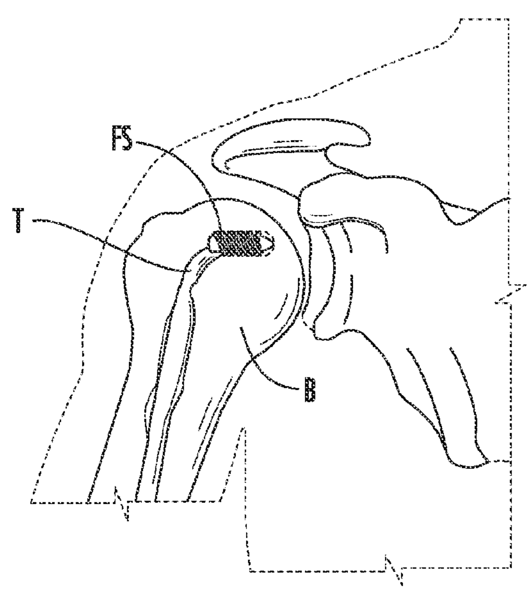

Following this, as shown in FIG. 8, the inserter 14 is withdrawn from the channel C and the guide 12 remains imbedded in the bone B. Next, as shown in FIGS. 9 and 10, a cannulated fixation screw FS, generally as mounted on a cannulated screw driver SD, is passed over the guide 12, and then rotated until fully seated into the bone B. Following this, as depicted in FIG. 11, the cannulated screw driver SD is removed from the guide 12. The guide 12 is then removed from the bone B and withdrawn from the surgical site, with the fixation screw FS secured into the bone B and securing the biceps tendon T to the bone B. The surgical site may then be closed to complete the biceps tenodesis procedure.

Figure 12:
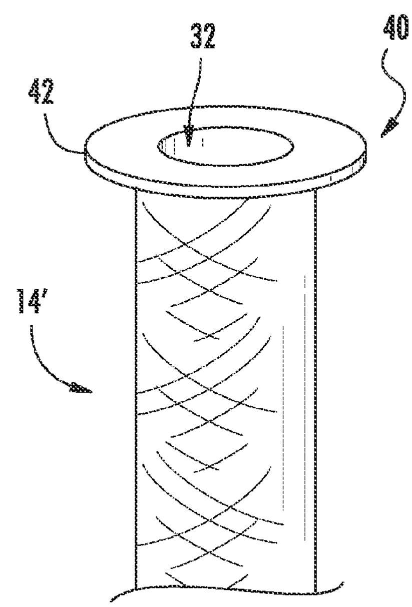
FIG. 12 shows a distal end of an alternate embodiment of an inserter.
Figure 13:
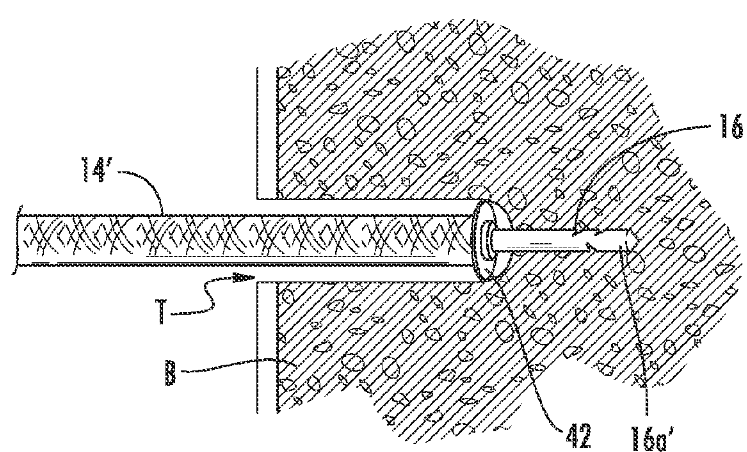
FIG. 13 shows use of the inserter of FIG. 12.

With reference to FIG. 12, there is shown a distal end 40 of an inserter 14' in accordance with an alternate embodiment. The inserter 14' is substantially similar to the inserter 14, except the distal end 40 of the inserter 14' at the entrance to the bore 32 is configured to have an enlarged diameter lip 42. The lip 42 is configured to provide an enlarged area to serve as a stop for inserting the guide 12 into the bone. This is advantageous to enable a repeatable and consistent depth of penetration of the guide 12 and to avoid having the distal end of the inserter become embedded in bone B, such as shown in FIG. 13. The lip 42 also serves to facilitate or encourage the tendon into the channel.

The apparatus and methods described herein for arthroscopic tenodesis are advantageous in that they do not require a dedicated interference screw or fixation device, but enable use of a wide variety of cannulated interference screws. The apparatus and methods also advantageously enable temporary fixation of the tendon to the bone, avoid the need for any implant beyond the fixation screw, improve surgeon visibility, and reduce operating room time and costs by reducing the number of steps required as compared to conventional tenodesis procedures.

The foregoing description of preferred embodiments for this disclosure has been presented for purposes of illustration and description. The description and embodiments are not intended to be exhaustive or to limit the disclosure to the precise forms disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. An arthroscopic tenodesis kit for use in installing a cannulated fixation screw for attaching a tendon to a bone without the need to utilize suture material for attaching the tendon to bone, comprising:

a guide consisting essentially of an elongate member having a length with a distal portion having a plurality of angled slots configured to directly and releasably engage a tendon; and an inserter comprising an elongate cannulated body having an interior bore having a blind end and an open end configured to slidingly receive the guide, the body of the inserter having a length that is shorter than the length of the guide, so that the distal portion of the guide remains spaced from the bore when the guide is fully received within the bore.

2. The kit of claim 1, wherein the angled slots are configured as acute angles oriented to open toward a distal end of the guide.

3. The kit of claim 2, wherein the angled slots have an angle of opening of from about 45 to about 70 degrees.

4. The kit of claim 1, wherein the slot comprises a plurality of slots staggered along the distal portion of the guide, such that no slot is exactly opposite another of the slots.

5. The kit of claim 1, wherein the open end of the inserter is configured to have an enlarged diameter lip.

6. A method for performing arthroscopic tenodesis on a joint having a tendon, comprising the steps of:

a. severing the tendon;

b. using a guide consisting essentially of an elongate member having a length with a distal portion having at least one slot configured to directly engage the tendon, and directly engaging the tendon with the slot;

c. forming a tunnel or channel into the joint from a location at the outside of the joint to a bone within the joint;

d. using the guide to urge the tendon down the tunnel or channel to the bone;

e. applying force to the guide to imbed an end of the guide into the bone;

f. sliding a cannulated fixation screw along the guide to the bone and rotating the fixation screw to seat the fixation screw into the bone and fix the tendon to the bone;

g. releasing the tendon from the guide; and h. removing the guide in its entirety from the bone and withdrawing the guide in its entirety from the joint.

7. The method of claim 6, wherein the steps of using the guide to urge the tendon down the tunnel or channel to the bone and applying force to the guide to imbed an end of the guide into the bone, comprises seating the guide within an elongate cannulated body and applying force to the cannulated body to urge the guide down the tunnel or channel and to imbed the end of the guide into the bone.

8. A method for performing arthroscopic tenodesis on a body portion having a tendon and a bone, comprising the steps of:

a. severing the tendon;

b. using a guide consisting essentially of an elongate member having a length with a distal portion having a slot configured to directly engage the tendon, and engaging the tendon with the slot;

c. forming a tunnel or channel into the bone;

d. using the guide to directly engage the tendon and urge the tendon down the tunnel or channel to the bone;

e. sliding a cannulated fixation screw along the guide to the bone and rotating the fixation screw to seat the fixation screw into the bone and fix the tendon to the bone;

f. releasing the tendon from the guide; and g. removing the guide in its entirety from the body portion.

* * * * *